United States Patent
Lou et al.

(10) Patent No.: US 12,383,184 B2
(45) Date of Patent: Aug. 12, 2025

(54) LATE ACTIVATION OF CARDIAC SIGNALS

(71) Applicant: CARDIOINSIGHT TECHNOLOGIES INC., Independence, OH (US)

(72) Inventors: Qing Lou, Solon, OH (US); Timothy G. Laske, Shoreview, MN (US); Qingguo Zeng, Solon, OH (US); Ryan M. Bokan, Boise, ID (US); Koonlawee Nademanee, Los Angeles, CA (US)

(73) Assignee: CARDIOINSIGHT TECHNOLOGIES INC., Independence, OH (US)

( * ) Notice: Subject to any disclaimer, the term of this patent is extended or adjusted under 35 U.S.C. 154(b) by 500 days.

(21) Appl. No.: 17/669,832

(22) Filed: Feb. 11, 2022

(65) Prior Publication Data

US 2022/0287615 A1    Sep. 15, 2022

Related U.S. Application Data

(60) Provisional application No. 63/160,077, filed on Mar. 12, 2021.

(51) Int. Cl.
*A61B 5/364*   (2021.01)
*A61B 5/00*    (2006.01)
(Continued)

(52) U.S. Cl.
CPC ............ *A61B 5/364* (2021.01); *A61B 5/339* (2021.01); *A61B 5/355* (2021.01); *A61B 5/367* (2021.01);
(Continued)

(58) Field of Classification Search
CPC ...................................................... A61B 5/364
(Continued)

(56) References Cited

U.S. PATENT DOCUMENTS 4,422,459 A   12/1983   Simson
4,458,691 A   7/1984    Netravali
(Continued)

FOREIGN PATENT DOCUMENTS

CA   2242360 C   3/2009
EP   1070480 A2  1/2001
(Continued)

OTHER PUBLICATIONS

Thom F. Oostendorp et al., The Surface Laplacian of the Potential: Theory and Application. Apr. 1996, IEEE Transactions on Biomedial Engineering, vol. 43, No. 4. (Year: 1996).*
(Continued)

*Primary Examiner* — Nicole F Johnson
(74) *Attorney, Agent, or Firm* — Tarolli, Sundheim, Covell & Tummino LLP

(57) ABSTRACT

In a described example, a method includes identifying, by a processor, negative deflections of at least one unipolar signal representing cardiac electrical activity on a surface of interest during a respective interval of the at least one signal. The method also includes determining, by a processor, an activation time for a last identified negative deflection in the respective interval. The method also includes detecting, by the processor, an instance of late activation based on comparing the activation time to a temporal threshold.

32 Claims, 5 Drawing Sheets

(51) Int. Cl.
*A61B 5/339* (2021.01)
*A61B 5/355* (2021.01)
*A61B 5/367* (2021.01)
*G16H 20/30* (2018.01)
*G16H 40/63* (2018.01)

(52) U.S. Cl.
CPC .......... *A61B 5/4836* (2013.01); *A61B 5/7203* (2013.01); *G16H 20/30* (2018.01); *G16H 40/63* (2018.01)

(58) Field of Classification Search
USPC .......................................................... 60/516
See application file for complete search history.

(56) References Cited

U.S. PATENT DOCUMENTS

| | | | |
|---|---|---|---|
| 4,492,235 | A | 1/1985 | Sitrick |
| 5,054,496 | A | 10/1991 | Wen et al. |
| 5,092,341 | A | 3/1992 | Kelen |
| 6,574,492 | B1 | 6/2003 | Ben-Haim et al. |
| 6,941,165 | B2 | 9/2005 | Nakai et al. |
| 7,245,962 | B2 | 7/2007 | Ciaccio et al. |
| 8,478,393 | B2 | 7/2013 | Ramanathan et al. |
| 8,700,139 | B2 | 4/2014 | Blomqvist |
| 8,838,203 | B2 | 9/2014 | Van Dam et al. |
| 8,972,228 | B2 | 3/2015 | Ghosh et al. |
| 9,427,169 | B2 | 8/2016 | Zeng et al. |
| 9,610,023 | B2 | 4/2017 | Dubois et al. |
| 9,820,666 | B2 | 11/2017 | Bokan et al. |
| 9,826,915 | B2 | 11/2017 | Ramanathan et al. |
| 9,901,271 | B2 | 2/2018 | Deno |
| 9,974,462 | B2 | 5/2018 | Jayan et al. |
| 10,959,638 | B2 | 3/2021 | Dubois et al. |
| 11,179,112 | B2 | 11/2021 | Li et al. |
| 11,284,830 | B2 | 3/2022 | Lou et al. |
| 2002/0151808 | A1 | 10/2002 | Schwartzman et al. |
| 2007/0161915 | A1 | 7/2007 | Desai |
| 2009/0088655 | A1 | 4/2009 | Vajdic et al. |
| 2015/0032014 | A1 | 1/2015 | Ghosh |
| 2017/0246460 | A1 | 8/2017 | Ghosh |
| 2018/0296167 | A1 | 10/2018 | Stewart et al. |
| 2019/0030332 | A1* | 1/2019 | Ghosh .................. A61N 1/3603 |
| 2020/0260978 | A1 | 8/2020 | Ramanathan et al. |

FOREIGN PATENT DOCUMENTS

| | | |
|---|---|---|
| EP | 3021744 B1 | 2/2018 |
| EP | 3007763 B1 | 10/2018 |
| EP | 3092943 B1 | 7/2020 |
| EP | 3692905 A1 | 8/2020 |
| WO | 199724983 A2 | 7/1997 |
| WO | 2006037172 A1 | 4/2006 |

OTHER PUBLICATIONS

Thom F. Oostendorp, et al.; "The Surface Laplacian of the Potential: Theory and Application"; IEEE Transactions on Biomedical Engineering, IEEE, USA, vol. 43, No. 4, Apr. 1, 1996; XP011006225; ISSN: 0018-9294; 12 pgs.; DOI:10.1109/10.486259.

Applicant: Cardioinsight Technologies Inc.; "Late Activation of Cardiac Signals"; International Application No. PCT/US2022/019886; PCT International Search Report and Written Opinion; Authorized Officer: Juan Faymann; Jun. 29, 2022; 12 pgs.

* cited by examiner

LATE ACTIVATION OF CARDIAC SIGNALS

CROSS REFERENCE TO RELATED APPLICATION

This application claims the benefit of U.S. Provisional Patent Application No. 63/160,077, filed 12 Mar. 2021, which is incorporated herein by reference in its entirety.

FIELD

The present technology is generally related to detection and analysis of late activation of cardiac signals.

BACKGROUND

The normal electrical conduction of the heart allows electrical propagation to stimulate the myocardium. Time ordered stimulation of the myocardium allows efficient contraction of all four chambers of the heart, thereby allowing selective blood flow through both the lungs and systemic circulation. The ordered stimulation can become de-synchronized and thereby adversely affect the mechanical function of the heart. Various approaches exist to collect heart rhythm information, such as including invasive electrophysiology studies (e.g., invasive catheter mapping) and non-invasive methods (e.g., electrocardiograms and non-invasive electroanatomic mapping). Cardiac mapping of activation can be used to underscore the heart region of late activation, which contributes to the irregular heart rhythm and de-synchronized contraction.

SUMMARY

The techniques of this disclosure generally relate to detection and analysis of late activation of cardiac signals.

In a described example, a method includes identifying, by a processor, negative deflections of at least one unipolar signal representing cardiac electrical activity on a surface of interest during a respective interval of the at least one signal. The method also includes determining, by a processor, an activation time for a last identified negative deflection in the respective interval. The method also includes detecting, by the processor, an instance of late activation based on comparing the activation time to a temporal threshold.

In another example, a system includes body surface electrodes adapted to be placed on an outer surface of a body of a patient to measure electrophysiological signals non-invasively. A computing device is configured to store data and execute machine readable instructions. The data can include electrophysiological data representing of cardiac electrophysiological activity for a plurality of points across at least one spatial region of a surface of a heart of a patient. The electrophysiological data can be reconstructed for the at least one spatial region of the heart that includes the plurality of points based on the non-invasively measured electrophysiological signals. The instructions executable to perform the method described above.

In yet another example, one or more non-transitory computer-readable media have instructions that, when executed by a processor, are programmed to perform a method. The method includes:
identifying negative deflections of electrophysiological signals representing cardiac electrical activity on a surface of interest during a respective time interval;
reducing reduce far-field components in the electrophysiological signals;
determining an activation time for a last identified negative deflection in each of the respective electrophysiological signals; and
detecting an instance of late activation for each of the respective electrophysiological signals based on comparing the activation time to a temporal threshold.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

This disclosure relates to detecting late activation in cardiac signals, such as may further be used to identify one or more regions (e.g., zones) of the heart exhibiting late activation.

Figure 1:
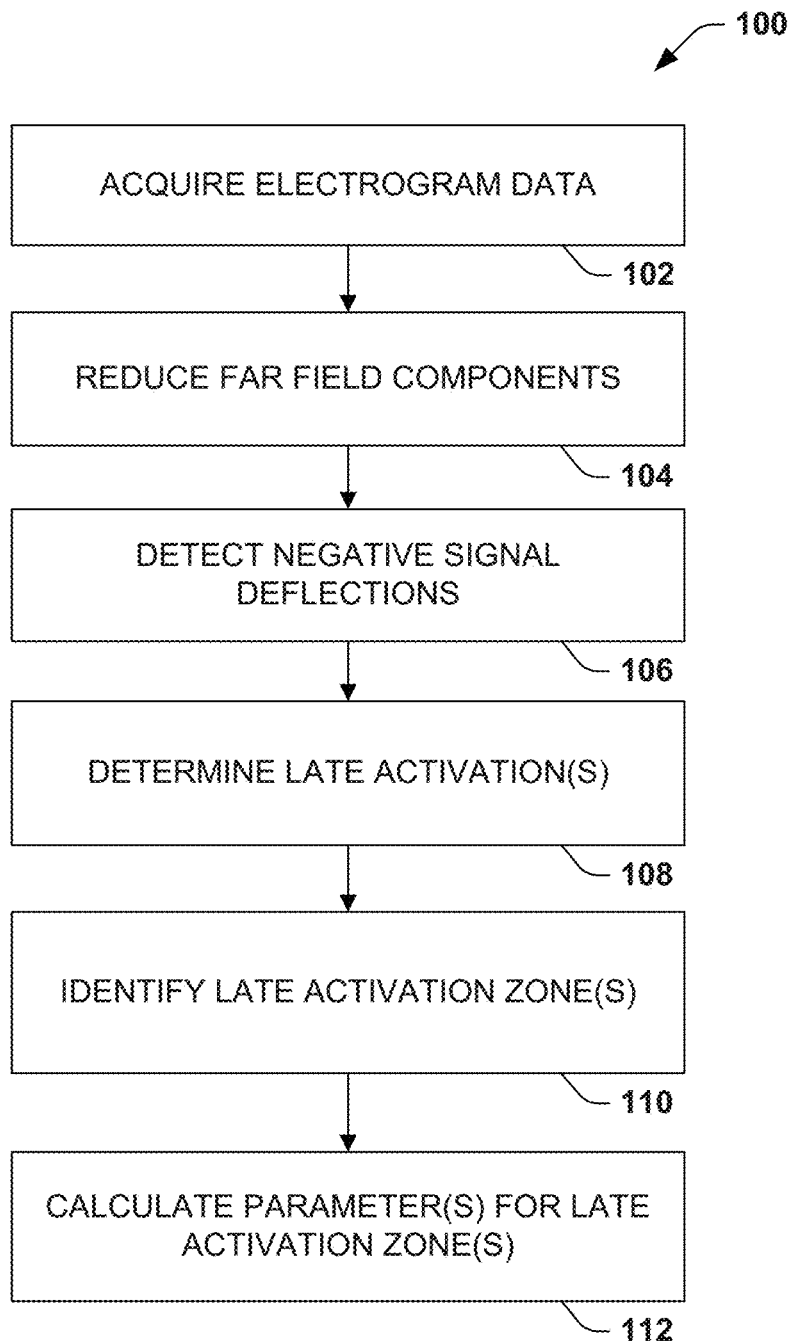
FIG. 1 is a flow diagram that illustrates an example method of detecting late activation for cardiac signals.

FIG. 1 depicts an example of a method 100 for detecting late activation in cardiac signals. While, for purposes of simplicity of explanation, the example method of FIG. 1 is shown and described as executing serially, it is to be understood and appreciated that the example method is not limited by the illustrated order, as some actions could in other examples occur in different orders, multiple times and/or concurrently from that shown and described herein. Additionally, some actions may be omitted from the method 100, as being optional. At least some portions of the method 100 can be implemented by hardware, software, or a combination of hardware and/or software, such as described herein (see, e.g., the system of FIG. 8).

In the example of FIG. 1, at 102, the method 100 includes acquiring electrophysiological (EP) signals for the heart. In an example, the electrophysiological signals acquired at 102 are unipolar signals, such as unipolar cardiac electrograms, across a surface of interest. In an example, the EP signals correspond to signals reconstructed on to the surface of interest based on electrical signals measured non-invasively by an arrangement of sensors, such as distributed across the patient's thorax. For example, a processor can solve an inverse problem to compute estimated values of the reconstructed cardiac signals on to points (e.g., nodes) distributed across the surface of interest. The processor may solve the inverse problem based on geometry data and electrical data representing non-invasive electrophysiological signals. The electrical data may be acquired from non-transitory memory where the signals are stored. Alternatively, or additionally, electrophysiological signals may be acquired in real-time (or near real-time) from a monitoring system having inputs coupled to sensors adapted to measure the EP signals from a body surface. For example, the surface of interest is a cardiac envelope, such as an epicardial surface, an endocardial surface, a combination of epicardial and endocardial surfaces of the patient's heart or another three-dimensional geometrical surface (e.g., a sphere or heart model).

At 104, the method includes processing the signals for the surface of interest to reduce the impact of far-field signal components on the respective signals, which effectively enhances the local signal components of the respective signals on the surface of interest. In an example, the processing implemented to reduce far-field components is applied globally to all the respective signals during one or more time intervals. In another example, processing implemented to reduce far-field components is applied selectively, reducing far-field components for the reconstructed signals for one or more spatial regions of the surface of interest.

As an example, the surface of interest (e.g., the entire heart or one or more chambers of the heart) may be divided into a plurality of different regions. Each region may be assigned a value representative of susceptibility to far-field components for the respective region. A susceptibility value thus can be determined for each of the respective spatial regions across the surface of interest. The susceptibility value may be a binary value (e.g., 0 or 1; on/off) to indicate whether or not to employ processing to reduce far-field components for the signals for each of the respective spatial regions. Alternatively, or additionally, the value may be determined as a discrete value or along a continuous scale to control (or vary) the amount by which far-field signal components are reduced for each of the respective spatial regions. The values may be assigned to respective spatial regions automatically (e.g., by instructions executed by a processor), such as based on a priori information or medical imaging data, or manually in response to a user input specifying values for the respective spatial regions. Regions determined to contain dense scar tissue tend to be subject to large far-field components. The right ventricular outflow tract (RVOT) and the left ventricular apex also are known to be subject to large far-field components. Thus, each of regions to which the processing is implemented to reduce far-field components can be assigned a value indicative of the region's susceptibility to far-field components. The assigned susceptibility values may be stored in memory, programmatically linked to each of the respective spatial regions. The stored susceptibility values thus may be employed at 104 to selectively reduce far-field components for signals (e.g., unipolar reconstructed EP signals) in each respective region across the surface of interest.

As a further example, reducing far-field signal components (at 104) is implemented by applying a surface Laplacian operator to the acquired signals (e.g., to unipolar reconstructed EP signals on the surface of interest). The surface Laplacian operator may be as follows:

$$L_s = \partial^2 \varphi / \partial n^2$$

An example of how the surface Laplacian may be applied to electrical data, including the acquired signals for the surface of interest (at 102), is described in Oostendorp, et al., *The Surface Laplacian of the Potential: Theory and Application*, IEEE Transactions on Biomedical Engineering, vol. 43, no. 4, (April 1996), pp. 394-405.

At 106, the method includes detecting negative deflections of the respective signals (e.g., signals components having negative slope) on the surface of interest during one or more time intervals of the respective signals. Each interval of a respective signal may include one or more negative deflections. The negative deflections may be determined for signals regardless of whether or not far-field components have been reduced for the respective signals. That is, the reduction of far-field components (at 104) may be applied only to some regions, all regions or omitted altogether from the method 100.

In a further example, the respective negative deflections (detected at 106) are compared to an amplitude threshold to confirm whether the deflection represents an actual activation. In this way, negative deflections that do not at least satisfy the amplitude threshold are discarded (e.g., discarded to remove deflections as noise). The amplitude threshold can have a fixed value or a value that varies spatially across the surface of interest. For example, the value of the amplitude threshold across the surface of interest depends on the susceptibility of the regions to far-field components. Thus, the amplitude threshold may vary spatially across the surface of interest, such as by varying the amplitude threshold depending on the assigned susceptibility value assigned to each of the respective regions. For example, the amplitude threshold for a given spatial region may be inversely proportional to the susceptibility value assigned to the given region. In this way, spatial regions subjected to larger far-field components have lower amplitude thresholds and spatial regions subjected to smaller far-field components can have higher amplitude thresholds.

At 108, a late activation time is determined for each interval of the respective signals across the surface as the latest negative deflection for each respective interval. Thus, where the amplitude threshold is applied (as described above), negative deflections corresponding to noise have been removed to provide a remaining set of one or more negative deflections from which the latest negative deflection is selected as containing the late activation for each of the respective signals. A late activation time is determined from the latest negative deflection (the latest signal component having negative slope) for each signal in each interval, regardless whether this negative slope contains the largest negative derivatives or not. This approach has better accuracy in identifying the late activation zone than an existing approach in which the largest negative derivative is used. In an example, the activation time may be determined as a midpoint of the latest negative deflection, which may be the midpoint in amplitude or time for the respective signal components. In another example, the activation time may be determined as the point along the latest negative deflection having the greatest negative slope (−dV/dt).

Figure 2:
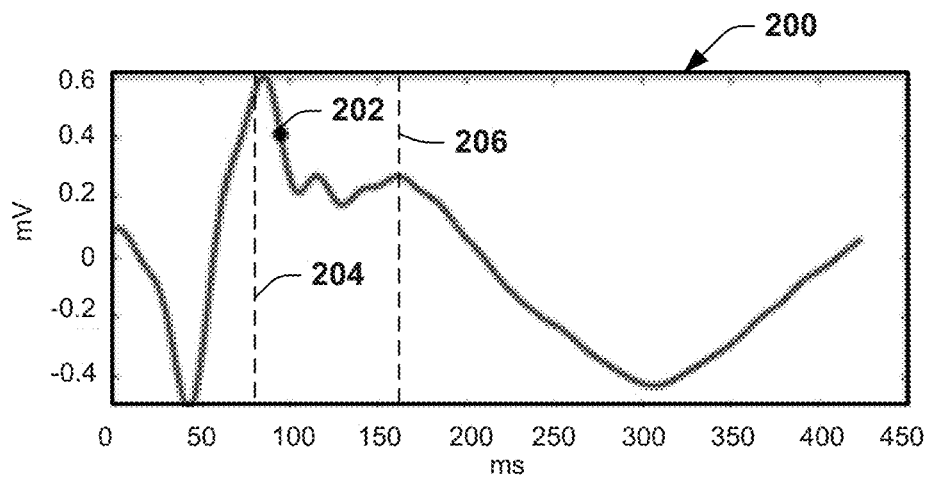
FIG. 2 is a plot that illustrates an example cardiac waveform with late activation.
Figure 3:
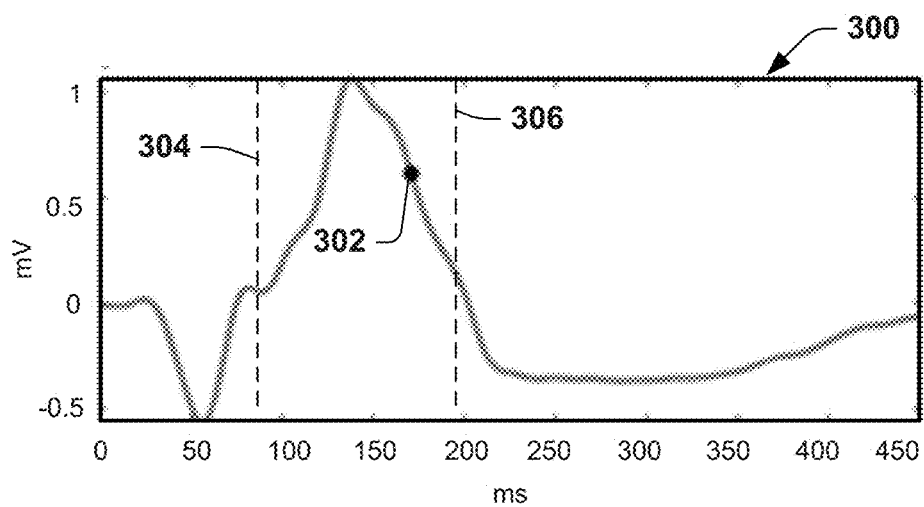
FIG. 3 is a plot that illustrates another example cardiac waveform with late activation.

FIGS. 2 and 3 depict example cardiac waveforms 200 and 300, respectively, for which respective instances of late activation 202 and 302 have been determined.

In some examples, a temporal threshold may also be applied to each of the late activations determined at 108 to filter out (e.g., remove or tag) late activation times determined for respective signals across the surface of interest that do not satisfy the temporal threshold. For example, if a respective late activation time is less than the temporal threshold, the respective late activation time does not constitute a late activation. Those late activation times that satisfy the temporal threshold can be classified (e.g., labeled by data stored in memory) as confirmed late activations. The temporal threshold may be fixed or variable (e.g., in response to a user input setting the temporal threshold to a desired time value). The minimum temporal threshold thus can be set to help ensure that late activation represents late activation for diseased tissue.

As an example, to define a temporal threshold, activation times are calculated (using the methods described herein) in control subjects who are known to be healthy (e.g., without heart disease). For example, a 95 percentile of the Gaussian distribution of the latest activation time (using the earliest activation in the heart surface as a reference time, time=0) in the control subjects with no heart disease is approximately 80 milliseconds. Thus, this value (e.g., 80 ms) can serve as the temporal threshold to identify pathologically late activations and late activation zones as described herein. In other examples, the temporal threshold may be determined according to other methods. An example temporal threshold is demonstrated at 204 and 304 in FIGS. 2 and 3, respectively. Because the instance of late activation 202, 302 occur after the threshold 204, 304, the late activation thus may represent a valid late activation.

A maximum time (e.g., an upper temporal bound or threshold) can also be set to remove (filter out) certain negative deflections that might indicate erroneous late activations (e.g., during repolarization of cardiac tissue). As described herein, each of the respective signals across the surface of interest is an interval of a cardiac waveform having Q, R, S and T wave components. In an example, the method thus can include detecting only negative deflections for a respective signal (determined at 106 for a respective interval—or at least the latest negative deflection determined at 108) that occur before an upper temporal bound for the signal interval. The upper temporal bound can be representative of a beginning of a signal feature. For example, the upper time bound for the respective interval is set for a given interval of a respective signal to indicate a beginning of the T-wave for the given interval. The upper bound thus can vary from interval to interval for each respective signal. In this way, negative deflections that may occur during cardiac repolarization are not included for purposes of determining late activation. An example upper bound, corresponding to the start of a T-wave, is demonstrated at 206 and 306 in each of FIGS. 2 and 3, respectively. Because the instance of late activation 202, 302 occur before its respective upper bound 206, 306, which is determined for each respective waveform 200, 300, the identified late activations are confirmed.

At 110, the method includes identifying one or more late activation zones (e.g., spatial areas across the surface of interest), which corresponds to a spatial region having one or more points in the respective region with one or more late activations. The late activation zone may correspond to a spatial area across the surface of interest exhibiting late activation (determined at 108) over a time interval. In an example, a minimum number of late activations can be defined in order to classify a respective area as a late activation zone. In an example, a late activation zone may be constructed from a set of one or more points distributed across the surface of interest determined (at 108) to exhibit late activation. A contiguous set of such points may be defined as belonging to the same late activation zone.

At 112, the method 100 includes calculating (or measuring) one or more parameters for each identified late activation zone. As mentioned, each late activation zone may include one or more points distributed across the surface of interest (e.g., a cardiac envelope). For example, the parameters calculated at 112 for each late activation zone may include an average activation time for the respective zone, an average voltage for the respective zone, a voltage elevation or depression for the respective zone (e.g., quantifying signal elevation or depression of ST portion of the unipolar signal) and/or a spatial area of late activation (e.g. size) of the respective zone. The values of one or more such parameters can then be used for purposes of potential risk stratification. Additionally or alternatively, the values of one or more such parameters can be utilized for quantifying a disease state for a region of the heart based on detecting at least one instance of late activation for the region of the heart. In some examples, the method further may include controlling delivery of a therapy (e.g., ablation, resynchronization, pacing etc.) to the area on the surface of interest (e.g., the late activation zone) exhibiting late activation. The control may be implemented by a processor providing machine readable instructions to a therapy deliver system or specifying parameters to a user for applying the therapy at one or more specified locations on the heart.

As a further example, the method may also include generating a graphical map based on the late activation zone(s) identified (at 110) across the surface of interest. The graphical map may be provided to the display to visualize one or more electrocardiographic maps as well as other electrical information derived from the reconstructed electrical signals, including based on any of the parameters measured or calculated for each of the late activation zones. For example, each late activation zone may be displayed on a graphical map of the heart. In such map, each late activation zone may be rendered according to a color scale based on the late activation time (or one or more other parameters calculated at 112 the respective zone). Alternatively, the late activation time (and/or other parameters) for each point across the late activation zone(s) may be mapped independently across the cardiac surface to provide a higher level of granularity.

Figure 4:
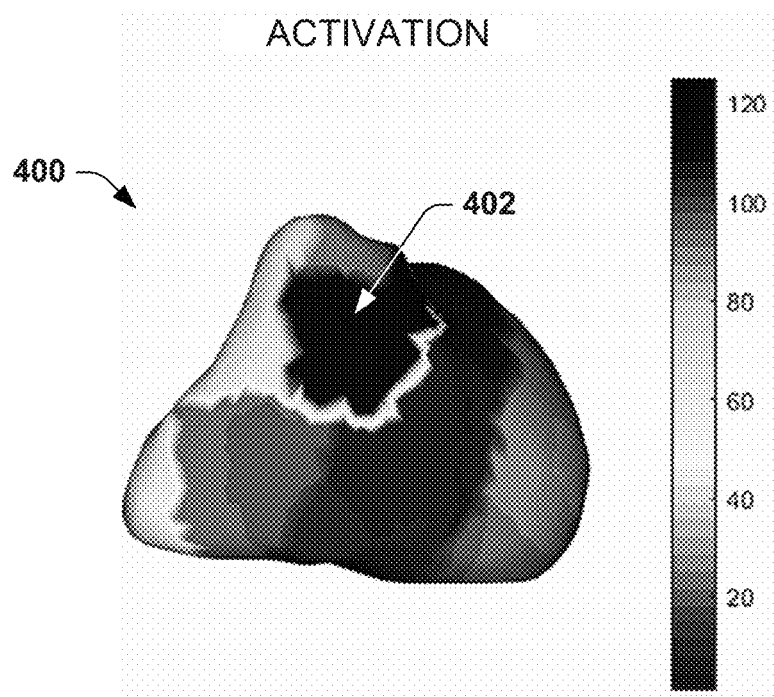
FIG. 4 is a graphical map that illustrates an example of an activation map.

FIGS. 4, 5, 6 and 7 depict examples of graphical maps that may be generated. FIG. 4 depicts an example of an activation map 400, showing a region of late activation at 402.

Figure 5:
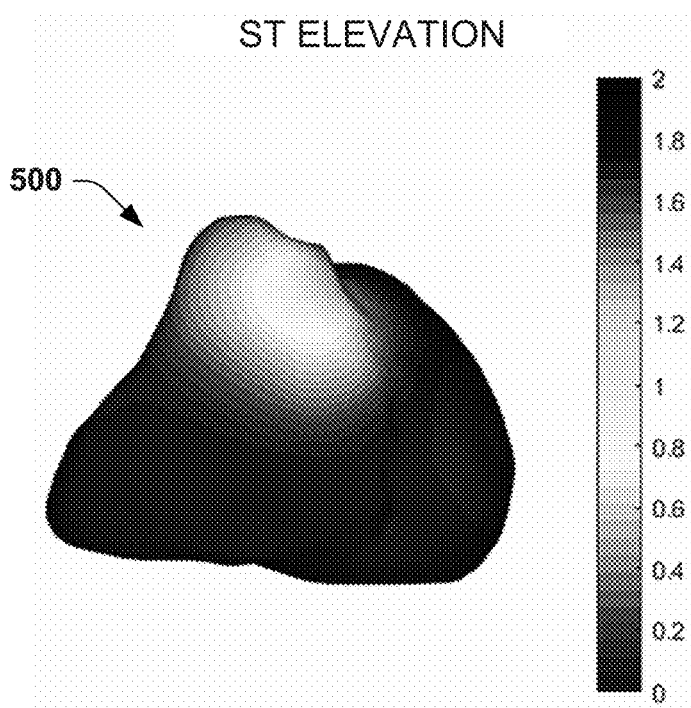
FIG. 5 is a graphical map that illustrates an example of an ST elevation map.

FIG. 5 depicts an example of an ST elevation map 500. For example, the ST elevation map 500 shows ST segment elevation across the cardiac surface. The ST elevation can be computed at respective points (e.g., nodes) on the cardiac surface over one or more respective cardiac cycles, which can be visualized on the map, such as depicted in FIG. 5.

Figure 6:
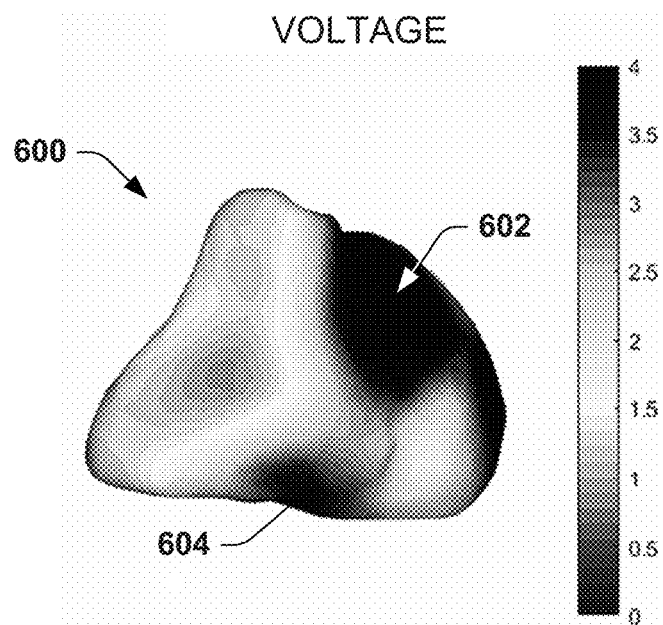
FIG. 6 is a graphical map that illustrates an example of a voltage map.

FIG. 6 depicts an example of a voltage map 600. For example, the voltage potential can be determined from reconstructed and/or invasively measured cardiac electrical signals and rendered on the cardiac surface for one or more cardiac cycles.

Figure 7:
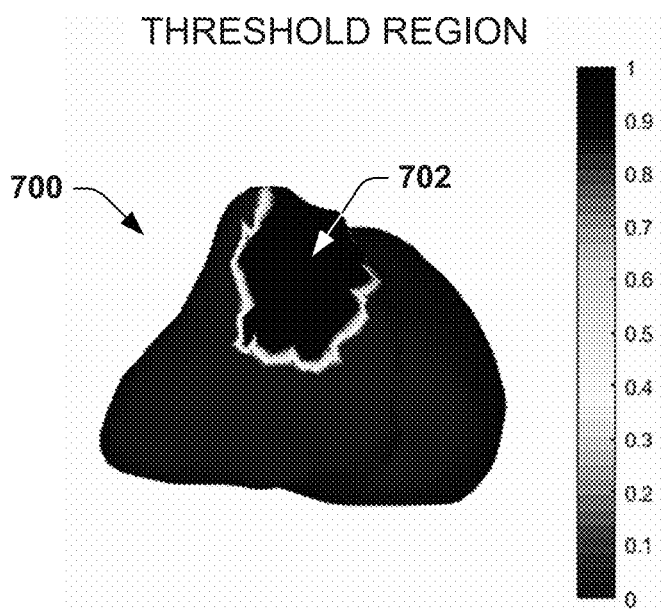
FIG. 7 is a graphical map that illustrates an example of a late-activation zone map for one or more regions of the heart.

FIG. 7 depicts an example of a late-activation zone map 700 for one or more regions of the heart. In the example of FIG. 7, a threshold can be applied to computed activation times to display a late activation region 702 (or multiple regions) having activation times that exceed the threshold. As described herein, the threshold can be user programmable, such as in response to a user input to set the threshold. The threshold can be varied to display respective changes in the map 700 such as to visualize one or more zones of late activation across the cardiac surface according to the selected threshold. For example, one or more thresholds thus can be used to identify respective different zones of late activation.

Figure 8:
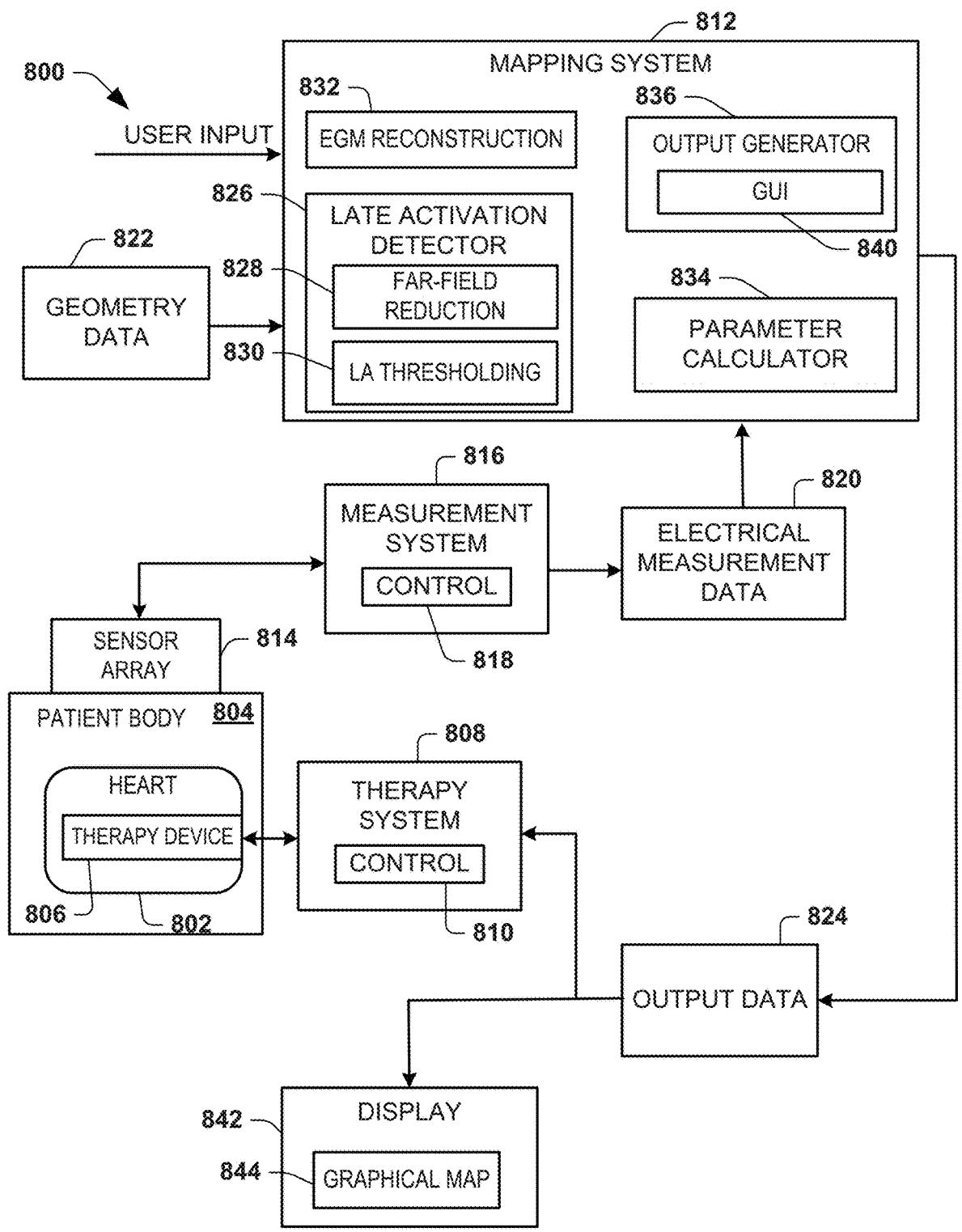
FIG. 8 depicts an example of a monitoring system.

FIG. 8 depicts an example of a system 800 that can be utilized to identify late activations for a patient's heart. In some examples, the system 800 can generate output data 824, which may be used to render a graphical map (e.g., a map on a heart model) 844 and/or display processed electrical signals on a display 842. The system 800 can also provide information in other formats to provide guidance to the user representative of and/or derived from detected late activations.

As disclosed herein, the system 800 has applications throughout various phases of patient care. As an example, the system can be used as part of a patient screening process, such as part of a patient risk stratification process (e.g., part of a diagnostic and/or treatment planning procedure). Additionally, the system 800 can be utilized as part of a treatment procedure, such as to determine parameters for delivering a therapy to the patient (e.g., delivery location, amount and type of therapy by one or more therapy system 808). The system 800 further may be used to perform post-treatment evaluation of the patient.

In the example of FIG. 8, the system 800 includes a sensor array 814 having one or more body surface electrodes that can be utilized for measuring patient electrical activity. As one example, the sensor array 814 can correspond to an arrangement of body surface sensors that are distributed over a portion of the patient's torso (e.g., thorax) for measuring electrical activity associated with the patient's heart. Examples of a body surface non-invasive apparatus that can be used as the sensor array 814 are shown and described in U.S. Pat. No. 9,655,561 and international publication No. WO 2010/054352. Other arrangements and numbers of sensing electrodes can be used as the sensor array 814, which may be set according to application requirements. For example, the array can be a reduced set of electrodes, which does not cover the patient's entire torso and is designed for measuring electrical activity for a particular purpose (e.g., an array of electrodes specially designed for analyzing atrial fibrillation and/or ventricular fibrillation) and/or for monitoring a predetermined spatial region of the heart. In some examples, the system 800 includes one or more sensors may also be located on a device 806 that is adapted to be inserted into the patient's body 804 and to measure electrophysiological signals invasively.

In each of such example approaches for acquiring patient electrical information, including invasively, non-invasively, or a combination of invasive and non-invasive sensing, the sensor array 814 provides the sensed electrophysiological information to a corresponding measurement system 816. The measurement system 816 can include corresponding controls 818 configured to provide electrophysiological measurement data 820 that describes electrical activity (e.g., ECG signals) detected by the sensors in the sensor array 814. For example, signal processing circuitry of the measurement system 816 can convert measured analog signal(s) to corresponding digital electrophysiological signals represented in the electrophysiological measurement data 820.

The control 818 can also be configured to control the data acquisition process for measuring electrical activity and providing the measurement data 820 (e.g., at a predefined sampling rate). In some examples, the control 818 can control acquisition of measurement data 820 separately from operation of the therapy system 808 (if implemented), such as in response to a user input. In other examples, the measurement data 820 can be acquired concurrently with and in synchronization with delivering therapy by the therapy system, such as to detect electrical activity of the heart 802 that occurs in response to applying a given therapy (e.g., according to therapy parameters). For instance, appropriate time stamps can be utilized for indexing the temporal relationship between the respective measurement data 820 and the therapy system 808 as to facilitate the evaluation and analysis thereof.

For example, a catheter, having one or more therapy delivery devices 806 affixed thereto can be inserted into the body 804 as to contact the patient's heart 802, endocardially or epicardially. Various types and configurations of therapy delivery devices 806 that can be utilized, which can vary depending on the type of treatment and the procedure. For instance, the therapy device 806 can be configured to deliver electrical therapy, chemical therapy, sound wave therapy, thermal therapy or any combination thereof.

By way of further example, the therapy delivery device 806 can include one or more electrodes located at a tip of an ablation catheter configured to generate heat for ablating tissue in response to electrical signals (e.g., radiofrequency energy) supplied by a therapy system 808. In other examples, the therapy delivery device 806 can be configured to deliver cooling to perform ablation (e.g., cryogenic ablation), to deliver chemicals (e.g., drugs), ultrasound ablation, high-frequency radiofrequency ablation, pulsed field ablation, non-invasive ablation or a combination thereof. In still other examples, the therapy delivery device 806 can include one or more electrodes located at a tip of a pacing catheter to deliver electrical stimulation, such as for pacing the heart, in response to electrical signals (e.g., pacing current pulses) supplied by a therapy system 808. Other types of therapy can also be delivered via the therapy system 808 and the invasive therapy delivery device 806 that is positioned within the body.

As a further example, the therapy system 808 can be located external to the patient's body 804 and be configured to control therapy that is being delivered by the device 806. For instance, the therapy system 808 includes a control system (e.g., hardware and/or software) 810 that can communicate (e.g., supply) electrical signals via a conductive link electrically connected between the delivery device (e.g., one or more electrodes) 806 and the therapy system 808. The control system 810 can control parameters of the signals supplied to the device 806 (e.g., current, voltage, repetition rate, trigger delay, sensing trigger amplitude) for delivering therapy (e.g., ablation, stimulation, etc.) via electrode(s) of the therapy device 806 to one or more locations of the heart 802. The control system 810 can set the therapy parameters and apply stimulation based on automatic, manual (e.g., user input) or a combination of automatic and manual (e.g., semiautomatic controls). One or more sensors (not shown) of the device 806 can also communicate sensor information back to the therapy system 808. The position of the device 806 relative to the heart 802 can be determined and tracked intraoperatively via an imaging modality (e.g., fluoroscopy, X ray), a mapping system 812, direct vision, a localization system or the like. The location of the device 806 and the therapy parameters thus can be combined to determine corresponding therapy delivery parameters.

The mapping system 812 is programmed to combine the electrophysiological measurement data 820 corresponding to sensed body surface electrical activity of the heart 802 to generate corresponding output data 824. As described herein, the output data 824 can represent or characterize electrophysiological signals on a surface of interest (e.g., on the body surface, a cardiac envelope on or within the heart 802). The mapping system 812 may further generate the output data 824 to represent information derived from the measured electrophysiological signals, including a representation of late activation of cardiac signals on a surface of interest, as disclosed herein.

For example, the system 800 includes electrogram reconstruction 832 programmed to compute an inverse solution and provide corresponding reconstructed electrograms across the surface of interest based on the electrophysiological measurement data 820 and geometry data 822. For example, the geometry data 822 can correspond to a mathematical model, such as can be a generic model or a model that has been constructed based on image data obtained for the patient (e.g., via an imaging modality, such as CT, MRI, bi-plane X ray or the like) and provides spatial coordinates for the patient's heart 802 and electrodes on the sensor array. The reconstructed electrograms thus can correspond to electrocardiographic activity across a surface of interest, such as a cardiac envelope, and can include static (three-dimensional at a given instant in time) and/or be dynamic (e.g., four-dimensional map that varies over time). Examples of inverse algorithms that can be implemented by the EGM reconstruction 832 include those disclosed in U.S. Pat. Nos. 7,983,743 and 6,772,004. The EGM reconstruction 832 thus is programmed reconstruct the body surface electrical activity measured via the sensor array 814 onto a multitude of locations on a cardiac surface of interest (e.g., greater than 1,000 locations, such as about 2,000 locations or more). In other examples, the mapping system 812 can compute electrical activity over a sub-region of the heart based on electrical activity measured invasively, such as via a basket catheter or other form of measurement probe (e.g., on or attached to device 806).

As a further example, the mapping system 812 includes a late activation detector 826 programmed to detect instances of late cardiac activation across the surface of interest. In an example, the late activation detector 826 determines the instances of late activation across the surface of interest the reconstructed electrophysiological signals (e.g., unipolar EP signals) computed by the EGM reconstruction 832. In other examples, the late activation detector 826 determines instances of late activation from other electrophysiological signal measurements.

For example, the late activation detector 826 is programmed to perform the method 100 of FIG. 1 and determine instances of late activation across the surface of interest. Thus, in the example of FIG. 8, the late activation detector 826 includes a far-field reduction function 828 and late activation thresholding function 830. The far-field reduction function 828 is programmed to reduce the impact of far-field signal components on the electrophysiological signals, such as described herein. The late activation detector 826 is programmed to detect negative deflections for one or intervals of the respective eletrophysiological signals. The thresholding function 830 may be programmed to apply one or more temporal thresholds and/or an amplitude threshold, as described herein. The late activation detector 826 may determine instances of late activation across the surface of interest based on the far-field reduction and/or thresholding that is applied. As described herein, each of the far-field reduction function 828 and/or thresholding function 830 may be applied globally to all signals or be applied in a spatially variable manner to selected signals across the surface of interest (e.g., based on a susceptibility to far-field components).

The mapping system 812 includes an output generator 836 to provide the output data 824 to visualize on the display 842 a graphical map or other information for one or more intervals of electrophysiological signals. Some examples of output displays that can be provided by the output generator 836 are disclosed with respect to FIGS. 4, 5, 6 and 7. The output generator 836 thus generates the output data 824 to display a graphical representation based on determined instances of late activation, such as including a late activation map across the surface of interest and/or parameters derived for one or more late activation zones. In some examples, the output generator 836 further may be configured to provide risk stratification (e.g., heart failure, sudden cardiac death) for a patient based on the information produced by the late activation detector 826. For example, the output generator 836 can categorize a type of treatment or protocol (e.g., resynchronization pacing, ablation, or implantable cardioverter-defibrillator) responsive to detecting instances of late activation and/or parameters derived from the late activation data.

The output generator 836 may also generate the output data 824 to display other types of information, such as time-domain plots, frequency-domain plots or the like. In some examples, the output generator 836 maps computed late activation data to a geometric surface of a heart model. As disclosed herein, the maps can be computed based on electrical data that is acquired non-invasively via one or more electrodes in the sensor array 814 distributed on the surface of the patient's body 804.

Since the measurement system 816 can measure electrical activity of a predetermined region of the torso or the entire torso concurrently (e.g., where the sensor array 814 including a plurality of electrodes covers the entire thorax of the patient's body 804), the resulting output data (e.g., ECG signals and/or electrocardiographic maps) 824 thus can also represent concurrent cardiac electrical data in a temporally and spatially consistent manner. Thus, instances of late activation may be identified for the entire heart surface over one or more time intervals. The time interval for which the output data/maps are computed can be selected based on user input, such as via GUI 840. Additionally or alternatively, the selected intervals can be synchronized with the application of therapy by the therapy system 808. Parameters associated with the graphical representation, corresponding to an output visualization of the computed map, such as including selecting a time interval, a type of information that is to be presented in the visualization and the like can be selected in response to a user input via the GUI 840.

Additionally, the output data 824 can be utilized by the therapy system 808, if included in the system 800. The control that is implemented can be fully automated control, semi-automated control (partially automated and responsive to a user input) or manual control based on the output data 824. In some examples, the control system 810 for the therapy system 808 can utilize the output data to control one or more therapy parameters. As an example, the control 810 can control delivery of ablation therapy to a site of the heart (e.g., epicardial or endocardial wall) based on late activation data that has been determined by the function 830, such as disclosed herein. For instance, the delivery of therapy can be terminated automatically in response to detecting the absence of cardiac (e.g., atrial) late activation after a time period. In other examples, an individual user can view the map generated in the display to manually control the therapy system based on information that is visualized. Other types of therapy and devices can also be controlled based on the output data 824.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A method, comprising:
    identifying, by a processor, negative deflections of at least one signal representing cardiac electrophysiological activity on a surface of interest during a respective interval of the at least one signal, wherein the negative deflections define portions of the at least one signal that have a negative slope;
    processing, by the processor, the negative deflections to exclude a subset of the negative deflections to provide a remaining set of negative deflections;
    identifying, by the processor, a last identified negative deflection of the remaining set of negative deflections in the respective interval;
    determining, by the processor, an activation time for the last identified negative deflection of the remaining set of negative deflections in the respective interval;
    detecting, by the processor, an instance of late activation in response to determining that the activation time satisfies a temporal threshold;
    identifying, by the processor, one or more late activation zones corresponding to one or more regions on the surface of interest; and
    providing, by the processor, a risk stratification for a patient in response to identifying the one or more late activation zones.

2. The method of claim 1, wherein the at least one signal comprises reconstructed cardiac signals representing the cardiac electrophysiological activity on the surface of interest, the reconstructed cardiac signals being reconstructed by the processor to points distributed across the surface of interest that define the one or more late activation zones based on non-invasive electrophysiological signals measured for at least the respective interval.

3. The method of claim 2, wherein the surface of interest comprises a cardiac envelope within a patient's body and the non-invasive electrophysiological signals are measured on an outer surface of the patient's body.

4. The method of claim 2, further comprising processing the reconstructed cardiac signals to reduce far-field components in the respective signals.

5. The method of claim 4, wherein processing the reconstructed cardiac signals comprises applying a surface Laplacian operator to the reconstructed cardiac signals to reduce the far-field components in the respective signals and thereby enhance local signal components.

6. The method of claim 4, wherein processing the reconstructed cardiac signals comprises selectively reducing far-field components for the reconstructed cardiac signals for one or more regions of the surface of interest determined to have an increased susceptibility to respective far-field components.

7. The method of claim 6, further comprising determining the increased susceptibility to far-field components for respective spatially across the surface of interest based on imaging data and/or tissue characteristics.

8. The method of claim 1, further comprising comparing a time of the instance of late activation relative to an upper time bound for the respective interval representative of a beginning of a signal feature.

9. The method of claim 8, wherein the upper time bound for the respective interval is representative of a beginning of a T-wave.

10. The method of claim 2, further comprising comparing the negative deflections to an amplitude threshold to and discarding negative deflections that do not at least satisfy the amplitude threshold to provide the remaining set of negative deflections.

11. The method of claim 10, wherein the amplitude threshold has a value that varies spatially across the surface of interest.

12. The method of claim 2, wherein the one or more regions on the surface of interest exhibit late activation and are identified based on respective instances of late activation detected across the surface of interest.

13. The method of claim 1, further comprising quantifying a disease state for a region of a heart based on detecting at least one instance of late activation for the region of the heart.

14. The method of claim 1, further comprising controlling delivery of a therapy to one or more regions of the heart based on the instance of late activation detected across the surface of interest.

15. The method of claim 1, further comprising generating a graphical map based on the instance of late activation detected across the surface of interest.

16. A system, comprising:
    body surface electrodes adapted to be placed on an outer surface of a body of a patient to measure electrophysiological signals non-invasively; and
    a computing device configured to store data and execute machine readable instructions, the data including electrophysiological data representing of cardiac electrophysiological activity for a plurality of points across at least one spatial region of a surface of a heart of the patient, the electrophysiological data being reconstructed for the at least one spatial region of the heart that includes the plurality of points based on the non-invasively measured electrophysiological signals, the instructions executable to perform a method comprising:
  identifying negative deflections of at least one signal representing cardiac electrophysiological activity on a surface of interest during a respective interval of the at least one signal, wherein the negative deflections define portions of the at least one signal that have a negative slope;
  processing the negative deflections to exclude a subset of the negative deflections to provide a remaining set of negative deflections;
  identifying a last identified negative deflection of the remaining set of negative deflections in the respective interval;
  determining an activation time for the last identified negative deflection of the remaining set of negative deflections in the respective interval; and
  detecting an instance of late activation in response to determining that the activation time satisfies a temporal threshold, wherein delivery of a therapy to one or more regions of the heart is controlled based on the instance of late activation.

17. The system of claim 16, wherein the at least one signal comprises reconstructed cardiac signals representing the cardiac electrophysiological activity on the surface of interest, the reconstructed cardiac signals being reconstructed to points distributed across the surface of interest based on non-invasive electrophysiological signals measured for at least the respective interval.

18. The system of claim 17, wherein the instructions are further programmed to process the reconstructed cardiac signals to reduce far-field components in the respective signals.

19. The system of claim 18, wherein the instructions to process the reconstructed cardiac signals are further programmed to apply a surface Laplacian operator to the reconstructed cardiac signals to reduce the far-field components in the respective signals and thereby enhance local signal components.

20. The system of claim 18, wherein the instructions to process the reconstructed cardiac signals are further programmed to selectively reduce far-field components for the reconstructed cardiac signals for one or more regions of the surface of interest determined to have an increased susceptibility to respective far-field components.

21. The system of claim 20, wherein the instructions are further programmed to determine the increased susceptibility to far-field components for respective spatially across the surface of interest based on imaging data and/or tissue characteristics.

22. The system of claim 16, wherein the instructions are further programmed to compare a time of the instance of late activation relative to an upper time bound for the respective interval representative of a beginning of a signal feature.

23. The system of claim 22, wherein the upper time bound for the respective interval is representative of a beginning of a T-wave.

24. The system of claim 17, wherein the instructions are further programmed to compare the negative deflections to an amplitude threshold to and discard negative deflections that do not at least satisfy the amplitude threshold to provide the remaining set of negative deflections.

25. The system of claim 24, wherein the amplitude threshold has a value that varies spatially across the surface of interest.

26. The system of claim 17, wherein the instructions are further programmed to identify one or more regions on the surface of interest exhibiting late activation based on respective instances of late activation detected across the surface of interest.

27. The system of claim 16, wherein the instructions are further programmed to quantify a disease state for a region of the heart based on detecting at least one instance of late activation for the region of the heart.

28. The system of claim 16, wherein the instructions are further programmed to control the delivery of the therapy to the heart based on instances of late activation detected across the surface of interest.

29. The system of claim 16, wherein the instructions are further programmed to generate a graphical map based on the instance of late activation detected across the surface of interest.

30. The system of claim 16, further comprising a therapy system, wherein the computing device is configured to control the therapy system based on one or more detected instances of late activation to deliver the therapy.

31. The system of claim 16, wherein the measured electrophysiological signals are unipolar signals.

32. One or more non-transitory computer-readable media having instructions that, when executed by a processor, are programmed to perform a method, comprising:
  identifying negative deflections of electrophysiological signals representing cardiac electrophysiological activity on a surface of interest during a respective time interval, wherein the negative deflections define portions of the at least one signal that have a negative slope;
  processing the negative deflections to exclude a subset of the negative deflections to provide a remaining set of negative deflections;
  identifying a last identified negative deflection of the remaining set of negative deflections in the respective interval;
  reducing far-field components in the electrophysiological signals;
  determining an activation time for the last identified negative deflection of the remaining set of negative deflections in each of the respective electrophysiological signals;
  detecting an instance of late activation for each of the respective electrophysiological signals in response to determining that the activation time satisfies a temporal threshold;
  determining, by the processor, a type of treatment protocol for a patient in response to detecting instances of late activation.

* * * * *